United States Patent [19]
Brady et al.

[11] Patent Number: 5,201,763
[45] Date of Patent: Apr. 13, 1993

[54] THIN INTRAOCULAR LENS

[75] Inventors: Dan G. Brady, Mission Viejo; Bernard F. Grisoni, Aliso Viejo; Christopher E. Doyle, Irvine, all of Calif.

[73] Assignee: Allergan, Inc., Irvine, Calif.

[21] Appl. No.: 843,527

[22] Filed: Feb. 28, 1992

[51] Int. Cl.$^5$ .............................................. A61F 2/16
[52] U.S. Cl. ...................................................... 623/6
[58] Field of Search ............................................ 623/6

[56] References Cited

U.S. PATENT DOCUMENTS

| | | |
|---|---|---|
| 3,284,406 | 11/1966 | Nelson . |
| 3,341,490 | 9/1967 | Burdick . |
| 3,457,214 | 7/1969 | Modic . |
| 3,992,355 | 11/1976 | Itoh et al. . |
| 3,996,187 | 12/1976 | Travnicek . |
| 3,996,189 | 12/1976 | Travnicek . |
| 4,380,643 | 4/1983 | Yoshida et al. . |
| 4,418,165 | 11/1983 | Polmanteer et al. . |
| 4,535,141 | 8/1985 | Kroupa . |
| 4,573,998 | 3/1986 | Mazzocco ............... 623/6 |
| 4,615,702 | 10/1986 | Koziol et al. ............ 623/6 |
| 4,647,282 | 3/1987 | Federov et al. .......... 623/6 X |
| 4,737,558 | 4/1988 | Falcetta et al. . |
| 4,785,047 | 11/1988 | Jensen . |
| 4,790,846 | 12/1988 | Christ et al. ............. 623/6 |
| 4,868,251 | 9/1989 | Reich et al. . |
| 4,878,912 | 11/1989 | Castleman .............. 623/6 |
| 4,882,398 | 11/1989 | Mbah . |
| 4,911,714 | 3/1990 | Poley ..................... 623/6 |

FOREIGN PATENT DOCUMENTS 1273144 8/1990 Canada .
0110537 6/1984 European Pat. Off. .

OTHER PUBLICATIONS

Saam, Formation of Linear Siloxane Polymers, 1990 American Chemical Society, pp. 71-89.
Grigoras et al, Conformational Analysis of Substituted Polysiloxane Polymers, 1990 American Chemical Society, pp. 125-144.
Rasoul et al, Thermal and Rheological Properties of Alkyl-Substituted Polysiloxanes, 1990 American Chemical Society, pp. 91-96.
Zaph et al, Synthesis and Properties of New UV-Curable Silicones with High Refractive Index, Polymeric Prints 30(2), p. 107 (1989).
Boutevin et al, Synthesis of Fluorinated Polysiloxanes. 8. Properties at Low and High Temperatures of Polysiloxanes with Fluoronated Grafts Macromolecules, vol. 24, (3), pp. 629–632 (Feb. 4, 1991).
Grigoras, Substituted Polysiloxane Polymers: Conformation of the Pendant Groups, Polymeric Prints, 31(1), 697(1990).
Fish et al, Ring Opening Polymerization of Cyclotetrasiloxanes with Large Substituents, pp. 36–37, Polymer Reprints, 31(1), Apr. 1990.
Christ et al, "Evaluation of the Chemical, Optical, and Mechanical Properties of Elastomeric Intraocular Lens Materials and Their Significance", J Cataract Refract Surg-vol. 15, Mar. 1989, pp. 176-184.
"Acrylens A Technical Evaluation of Foldable Intraocular Lenses", Ioptex Research Inc, copyright 1990.

Primary Examiner—Randall L. Green
Assistant Examiner—Mary Beth O. Jones
Attorney, Agent, or Firm—Gordon L. Peterson

[57] ABSTRACT

An intraocular lens for implantation in an eye comprising a deformable silicone optic configured so that the optic can be deformed to permit the intraocular lens to be passed through a scleral tunnel incision no longer than about 3.2 mm into the eye. The intraocular lens can be provided in a range of diopter powers. When the intraocular lens is implanted in the eye, the optic has sufficient rigidity to be substantially free of optical distortion resulting from force from the eye acting on the intraocular lens and the optic is of sufficient size to substantially prevent glare resulting from interaction of light and the periphery of the optic.

22 Claims, 3 Drawing Sheets

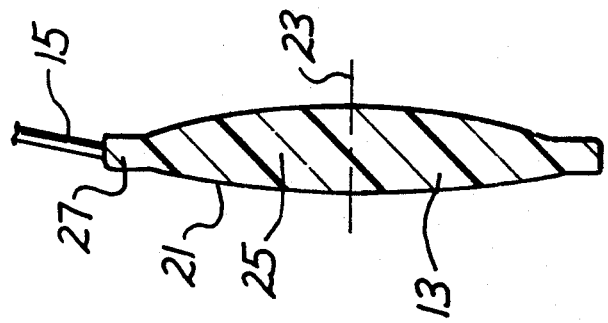
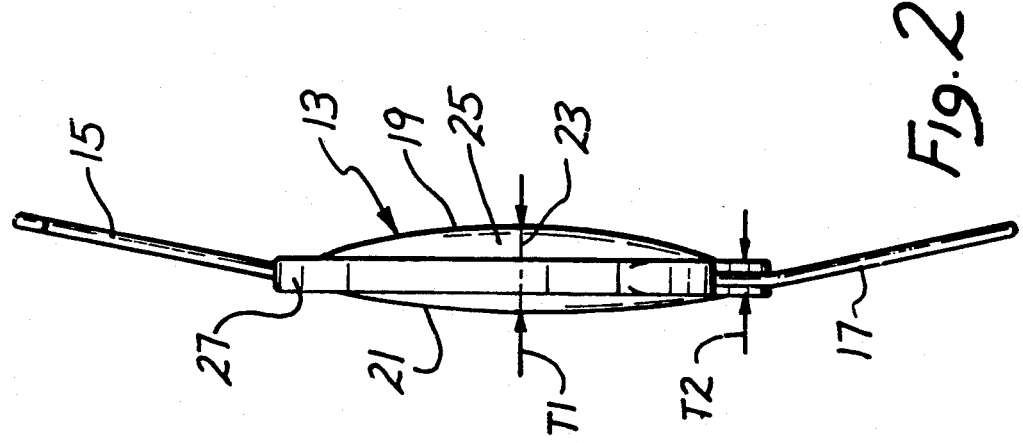
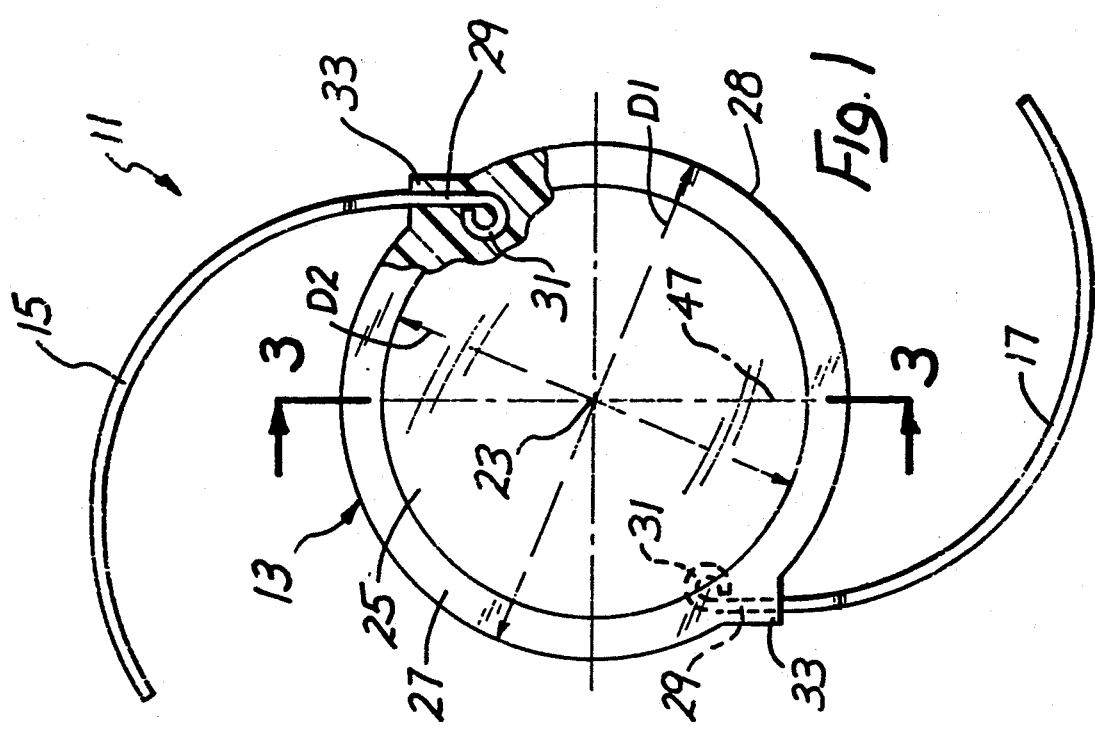

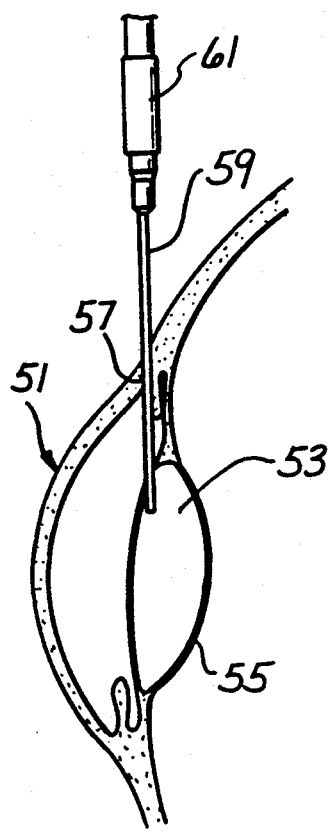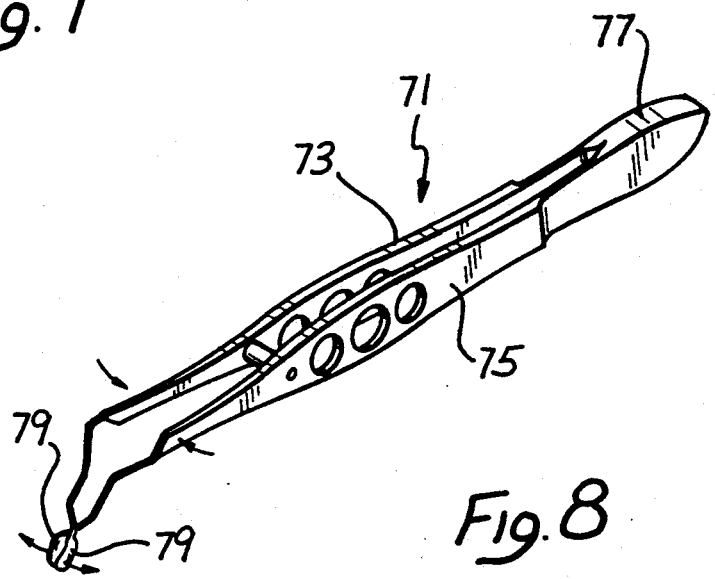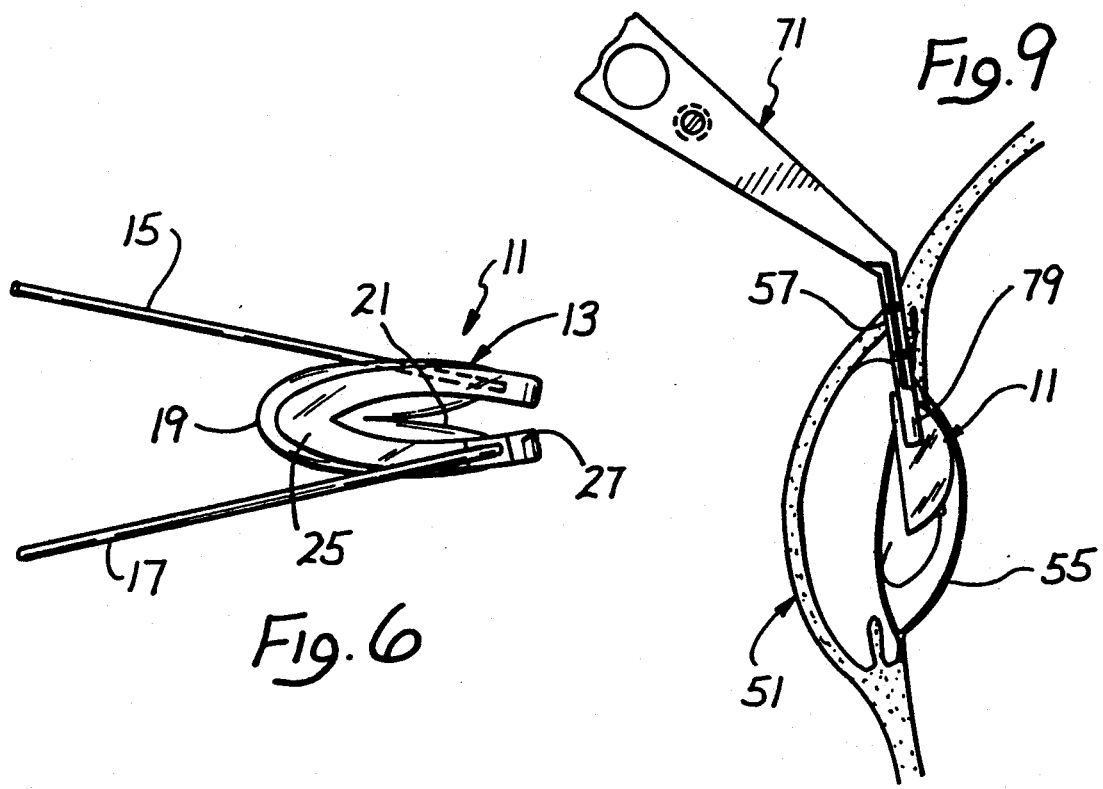

THIN INTRAOCULAR LENS

BACKGROUND OF THE INVENTION

1. Field of the Invention

This invention relates to an intraocular lens (IOL) and more particularly to an IOL with a deformable optic which enables the IOL to be passed through a scleral tunnel incision no longer than about 3.2 mm into the eye.

2. Background of the Invention

When the natural lens of the human eye becomes impaired through, for example, cataracts or injury, it is common practice to replace the natural lens with an IOL. One way to accomplish this is to form a relatively long incision in the eye and remove the natural lens in one piece. However, presently a much more common way to accomplish this is to form a shorter incision in the eye and insert a probe or a phaco tip of a phacoemulsification instrument through the incision into the eye to break up the natural lens using ultrasonic energy. The lens fragments are then aspirated from the eye through the relatively short phaco incision and the phaco tip is removed.

The length of the incision, which is commonly referred to as a phaco incision, in the eye through which the phaco tip is inserted is typically no greater than about 3.2 mm so that the phaco tip will fit somewhat snugly through the incision. It is generally recognized that the longer the lens-removal incision, the greater the trauma to the eye and the longer the patient recovery time. Other complications may also be caused by a large incision such as the need to remove the lens in one piece. About 80 percent of the lens-removal processes currently use phacoemulsification techniques. Of course, with only a small incision being needed for phacoemulsification lens extraction, it is desirable that IOL's be available and used that can be inserted through the small phaco incisions.

A typical IOL includes an optic, usually having a diameter of about 6 mm, and fixation members coupled to (or formed with) the optic to fix the optic within the eye in the region of the extracted lens. IOL's are of two basic types, those having a hard or rigid optic formed, for example, of polymethylmethacrylate (PMMA) and those having a deformable optic which is constructed of a deformable material such as silicone, hydrogel, or an acrylic. If a hard IOL is used, the 3.2 mm incision must be enlarged to approximately the diameter of the hard optic, in order to permit the hard optic to be inserted through the incision and much of the advantage of phacoemulsification lens extraction is thereby obviously lost.

There are two known classes of prior art IOL's which can be deformed (e.g., folded or rolled) to pass through a scleral tunnel incision of about 3.2 mm in length. A scleral tunnel incision is a single incision in the sclera without any additional incision which crosses or intersects the single incision. The first of these IOL's has an acrylic optic with a refractive index of about 1.47 or greater. The acrylic IOL's cover a full diopter range of about 12$d$ to about 24$d$, but do not have as high an elongation as is desired for IOL insertion through a 3.2 mm phaco incision. Elongation is defined as $(L_d/L_u)100$ where $L_d$ is the maximum change in length from the unstressed condition to the breaking point and $L_u$ is the unstressed length. A high elongation is desired so that the optic can be caused to resiliently stretch and flow to assume a small cross sectional configuration for passage through a small phaco incision. For example, a currently known acrylic optic may have an elongation of only about 150 percent.

The second of these classes of IOL's has a silicone based optic. In one known silicone based optic the refractive index is only about 1.408. Accordingly, it is necessary to have a relatively large maximum cross sectional area of about 5.1 square millimeters in order to provide an IOL of only 12 diopter power. Although higher diopter powers can be constructed with this silicone based material, the higher powers require a correspondingly greater maximum cross sectional area with the result that they will not ordinarily pass through a scleral tunnel incision of only about 3.2 mm in the eye. More specifically, the present inventors understand that it is highly unlikely that this type of silicone IOL is implantable through a 3.2 mm scleral tunnel incision in powers over 14$d$ and that in powers over 15$d$ implantation through a 3.2 mm scleral tunnel incision into the eye is essentially not possible. Implantation of an IOL of this type having a power of 20$d$ or greater is not possible.

A second kind of known silicone based optic is disclosed in Fedorov et al U.S. Pat. No. 4,647,282. One of the silicone based materials disclosed in this patent is said to have a refractive index of 1.480. However, this silicone based material has a percentage of elongation of only 130 percent, and the patent lacks, among other things, specific geometrical teachings as to how the optic is to be constructed.

A third kind of known silicone based optic is disclosed in copending application Ser. No. 562,452 filed on Aug. 1, 1990 (now abandoned) and entitled OPTICALLY CLEAR REINFORCED SILICONE ELASTOMERS OF HIGH OPTICAL REFRACTIVE INDEX AND IMPROVED MECHANICAL PROPERTIES FOR USE IN INTRAOCULAR LENSES. So far as the present inventors are aware, an IOL having an optic constructed of this silicone based material and having 16 diopter power or greater will not, without employing the principles of this invention as described hereinbelow, pass through a scleral tunnel incision of about 3.2 mm in length. At present, a known 16 diopter power optic of this material has a maximum cross sectional area of about 5.3 sq. mm.

SUMMARY OF THE INVENTION

This invention solves the problems noted above. For example, the IOL's of this invention include a resilient, deformable silicone based optic which has greater elongation than the known acrylic optics. In addition, the silicone based optic of this invention does not have any significant diopter power limitation. Although the IOL's of this invention have these advantages, they can also be inserted through a scleral tunnel incision of no longer than about 3.2 mm into the eye. Consequently, the phaco incision, which is commonly used for the phaco tip, need not be enlarged in order to permit the IOL to be implanted.

When an IOL of this invention is implanted in the eye, the optic has sufficient rigidity to be substantially free of optical distortion resulting from force from the eye acting on the IOL. The optic is also of sufficient size to substantially prevent the glare that would result if the dimensions of the optic were so small that light could interact with the periphery of the optic to cause glare.

The optic preferably has an elongation of at least about 200 percent. Preferably, the elongation of the optic is at least about 260 percent.

This invention is applicable to a very high percentage of the diopter powers currently being employed in IOL's. The invention is specifically applicable to deformable optics having from about 12 to about 24 diopter power, and this range of diopter powers is believed to be prescribed for about 95 percent of all IOL recipients. The features of this invention are applicable, for example, to an optic having at least about 20 diopter power, and this is a higher power than the diopter power of known prior art silicone IOL's that were implantable through a 3.2 mm scleral tunnel incision.

This invention is based, in part, upon the recognition by the present inventors that the maximum cross sectional area of the optic is a primary controlling factor in determining the length of the incision required for insertion of the deformable optic through the incision. More specifically, for insertion through a scleral tunnel incision of no greater than about 3.2 mm in length, the maximum cross sectional area of the optic should be no greater than about 4.4 square mm.

The optic of this invention has anterior and posterior faces, and the curvature of one or both of these faces determines the corrective or diopter power of the optic. In order to keep the maximum cross sectional area at or below the desired maximum, it is desirable to minimize the convex curvature of the face or faces which provide the correction. To obtain the necessary correction without undue convex curvature which would thicken the optic, it is preferred, but not essential, to employ an optic having an index of refraction of at least about 1.445 with an index of refraction of at least about 1.46 being preferred. An index of refraction less than 1.445 tends to limit the diopter correction that is obtainable or require other trade offs that may be undesirable.

It is also important that the optic not be made so thin that, when implanted and subjected to the usual forces from the eye, it buckles or deforms and thereby introduces optical distortion. For one preferred construction, the optic has an optical axis and the thickness of the optic along the optical axis is no less than about 0.736 mm in order to guard against the optical distortion that would result from mechanical deformation of the optic of the implanted IOL. Preferably this thickness is no less than about 0.813 mm.

The optic must also be of sufficient radial dimension to substantially prevent glare. To accomplish this, the optic should have sufficient radial dimensions to cover the optical zone within the eye to assure that light rays do not interact with the edges of the optic sufficiently to cause glare. In a preferred construction, the optic is circular and has a diameter of at least about 6 mm, although according to the FDA Tier System glare can be substantially prevented by an optic having smaller diameters down to about 5 mm.

Fixation members are used to fix the optic within the eye. Another important consideration is constructing the optic in a way that enables the obtaining of a strong attachment between the fixation members and the optic. This can advantageously be accomplished by constructing the optic so that it has a central optical zone and a peripheral zone circumscribing the optical zone. The peripheral zone is not used for focusing of light on the retina, but is used for receiving attachment regions of the fixation members for attaching the fixation members to the optic. The central optical zone is used for focusing light on the retina and providing the desired correction.

The peripheral zone also forms, in effect, a frame which assists in strengthening the optic against unwanted deformation after implantation. The peripheral zone preferably includes buttresses for use in attaching the fixation members to the optic and for lending support to the optic.

Because the peripheral zone adds to the maximum cross sectional area of the optic and does not contribute to the optical properties of the IOL, it is desirable to reduce the axial cross sectional area of the peripheral zone to a minimum. On the other hand, a certain thickness, i.e. axial dimension, of the peripheral zone is needed in order to form a strong attachment with the fixation members. In a preferred construction, the thickness of the peripheral zone in the axial direction is no less than about 0.305 mm with a thickness no less than about 0.381 mm being more preferred.

Other properties of interest of the optic include hardness and tensile strength. Preferably, the hardness of the optic is at least about 38 Shore A so that compressive forces exerted on the optic by the tool used for implanting the IOL is less likely to permanently scratch or mark the IOL. In addition, the optic preferably has a tensile strength of no greater than about 1000 psi because tensile strengths greater than this make the optic more difficult to elongate during insertion. The tensile strength should preferably be greater than about 600 psi in order to prevent mechanical distortion of the optic when the fixation members are resiliently urged radially inwardly.

Certain silicone based materials possess a number of properties which adapt them for use as the optic material. Preferably the silicone based materials are substantially free of acrylates. Preferred silicone based materials are described in copending application Ser. No. 562,452 filed on Aug. 1, 1990 (now abandoned) referred to above and entitled OPTICALLY CLEAR REINFORCED SILICONE ELASTOMERS OF HIGH OPTICAL REFRACTIVE INDEX AND IMPROVED MECHANICAL PROPERTIES FOR USE IN INTRAOCULAR LENSES. This application is incorporated by reference herein.

The fixation members can be of various configurations and material. For example, the fixation members may be constructed of PMMA or polypropylene. To more desirably apply the forces on the optic caused by the eye after implantation, each of the fixation members is preferably in the form of a C-shaped elongated resilient member. Preferably the fixation members are coupled to the optic at generally diametrically opposed locations.

The invention, together with additional features and advantages thereof may best be understood by reference to the following description taken in connection with the accompanying illustrative drawings.

BRIEF DESCRIPTION OF THE DRAWINGS

FIG. 1 is a plan view partially in section of a three piece IOL constructed in accordance with the teachings of this invention.

FIG. 2 is a side elevational view of the IOL of FIG. 1.

FIG. 3 is a sectional view taken generally along line 3—3 of FIG. 1.

FIG. 6 is an elevational view illustrating the IOL in a folded condition for insertion into the eye.

FIG. 7 is a perspective view illustrating the use of a phacoemulsification instrument to remove the natural lens of an eye.

FIG. 8 is a perspective view illustrating a representative form of insertion tool utilized for the deforming the IOL and inserting it through an incision into the eye.

FIG. 9 is a perspective view illustrating insertion of the IOL through the unlengthened phaco incision.

DESCRIPTION OF THE PREFERRED EMBODIMENT

Figure 4:
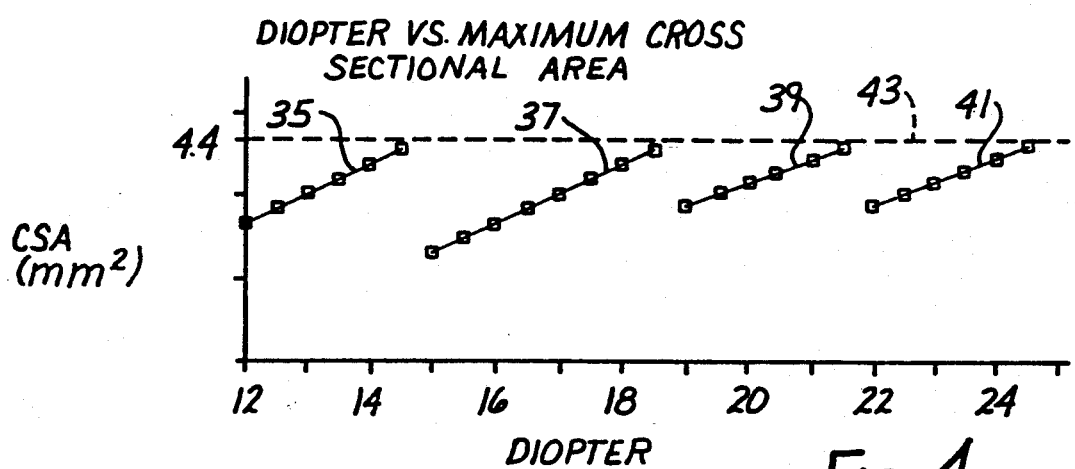
FIG. 4 is a plot of diopter power versus maximum cross sectional area for several groups of deformable IOL's.

FIGS. 1 and 2 show an IOL 11 which generally includes an optic 13 and identical fixation members 15 and 17. The optic 13 is resilient and deformable and preferably constructed (as by molding) of resilient deformable silicone based material having a refractive index of about 1.46, an elongation of about 260 percent, a tensile strength up to about 1000 psi and a Shore A hardness of about 38. Particularly useful silicone based materials are disclosed more fully below. Although various configurations may be employed for the optic 13, in the illustrated embodiment, the optic 13 is biconvex, is circular in plan and has an outer diameter D1 of about 6 mm.

The optic 13 has an anterior face 19 and posterior face 21. As illustrated, the faces 19 and 21 are both convex, and this is preferred. However, other configurations, such as plano-convex, which will yield the desired diopter power range, could alternatively be employed.

The various geometrical parameters for the optic 13 have been especially developed to enable the IOL 13 to be folded to a sufficiently small size to enable implantation through a scleral tunnel incision of no more than about 3.2 mm, and this is possible for optics having a range of diopter powers from about 12 to about 24. The optic 13 has an optical axis 23 and the thickness T1 of the optic 13 along the optical axis, i.e. the minimum center thickness, is no less than about 0.736 mm and preferably no less than about 0.813 mm. The optic 13 has central optical zone 25 with a diameter D2, an annular peripheral zone 27 circumscribing the optical zone and a periphery 28. The thickness T2 of the peripheral zone 27 in the axial direction, i.e. as viewed in FIG. 2, is preferably no less than about 0.381 mm although thickness as small as about 0.305 mm can be employed. The optical zone 25 is circular as viewed in plan (FIG. 1) and forms the lens portion or operative vision correction portion of the optic 13. The zones 25 and 27 are of integral, one-piece construction.

The optic 13 has a maximum cross sectional area which, in the embodiment illustrated, is the cross sectional area of the optic along a diameter. The maximum cross sectional area of the optic 13 is shown in cross section in FIG. 3 and is preferably no greater than about 4.4 square mm.

The peripheral zone 27 is a non-optical zone and does not form a part of the lens of the optic 13. The functions of the peripheral zone 27 include strengthening the optical zone 25 against deformation when implanted, mounting or attaching the fixation members 15 and 17 to the optic 13 and adding to the diameter of the optic 13 to reduce the likelihood of light interacting with the periphery 28 of the optic to cause glare after implantation.

Although the fixation members 15 and 17 may be of various different constructions, in this embodiment each of them is in the form of a generally C-shaped resilient fiber or strand of polypropylene. Each of the fixation members 15 and 17 has an attachment region 29 at its proximal end portion which is formed by shaping a portion of the proximal end portion of the fixation member into a loop 31. The material of the optic 13 completely surrounds the attachment regions 29 and fills the loops 31 to strongly attach the fixation members to the optic at diametrically opposed locations.

The IOL 11 can be made using an injection molding technique, and this as well as the use of the attachment loops 31, is described in Christ et al Pat. No. 4,790,846 which is incorporated by reference herein. Of course, various different techniques and constructions can be employed for providing some sort of fixation means for fixing the optic 13 in the eye, and the construction shown is merely illustrative.

The peripheral zone 27 preferably includes radial projections or buttresses 33 which receive a length of the attachment regions 29, respectively. The buttresses 33 aid the attachment of the fixation members 15 and 17 to the optic 13 and strengthen the optical zone 25 against deformation of the type that would create optical distortion in the eye.

The features of this invention typically enables the manufacture of a set of IOL's which are implantable through a scleral tunnel incision of no more than about 3.2 mm and which have from about 12 to about 24 diopter power. One preferred way of obtaining the desired features of this invention is to utilize a 6 mm diameter D1 optic of silicone based material or a material having a refractive index of at least 1.445, an elongation of at least about 200 percent and the parameters set forth in the table below.

| Positive Diopter Power | Peripheral Zone 27 Axial Thickness | Optical Zone 25 Diameter in Millimeters |
| --- | --- | --- |
| 12 to 14.5 | .457 mm | 5.5 mm |
| 15 to 18.5 | .381 mm | 5.5 mm |
| 19 to 21.5 | .381 mm | 5.25 mm |
| 22 to 24 | .381 mm | 5. mm |

FIG. 4 shows how the maximum cross sectional area (CSA of the optic 13 varies with diopter power. Specifically, FIG. 4 shows curves 35, 37, 39 and 41 for the four groups of positive diopter powers, respectively, in the table set forth above. Thus, by holding all other parameters of the optic 13 constant and changing the curvature of, for example, the anterior face 19, the cross sectional area CSA increases generally linearly as the diopter power is increased from 12 to about 14.5 as shown by the curve 35. As the maximum cross sectional area reaches the upper limit of about 4.4 square mm, which is shown by the upper limit line 43 in FIG. 4, other parameters of the optic 13 are changed in order to keep the maximum cross sectional area at or below the upper limit line 43. If the maximum cross sectional area of the optic 13 were allowed to go above the upper limit line 43, it would reduce the likelihood that the resulting IOL could be inserted through a scleral tunnel incision of no more than about 3.2 mm into the eye.

Although other parameters could be changed, in the embodiment defined by the above table, the axial thickness of the peripheral zone 27 was reduced from 0.457 mm to 0.381 mm for the diopter range of 15 to 18.5, and the variation of diopter and maximum cross sectional area in this diopter range is shown by the curve 37 in FIG. 4.

In order to not exceed the upper limit line 43 along the curve 37, the diameter D2 of the optical zone 25 is reduced to 5.25 mm, and this allows extension of the diopter range of 19 to 21.5 as shown by the curve 39. Similarly, by reducing the diameter D2 of the optical zone 25 to 5 mm, the diopter power range of 22 to 24 can be provided as shown by the curve 41 without exceeding the upper limit line 43.

Figure 5:
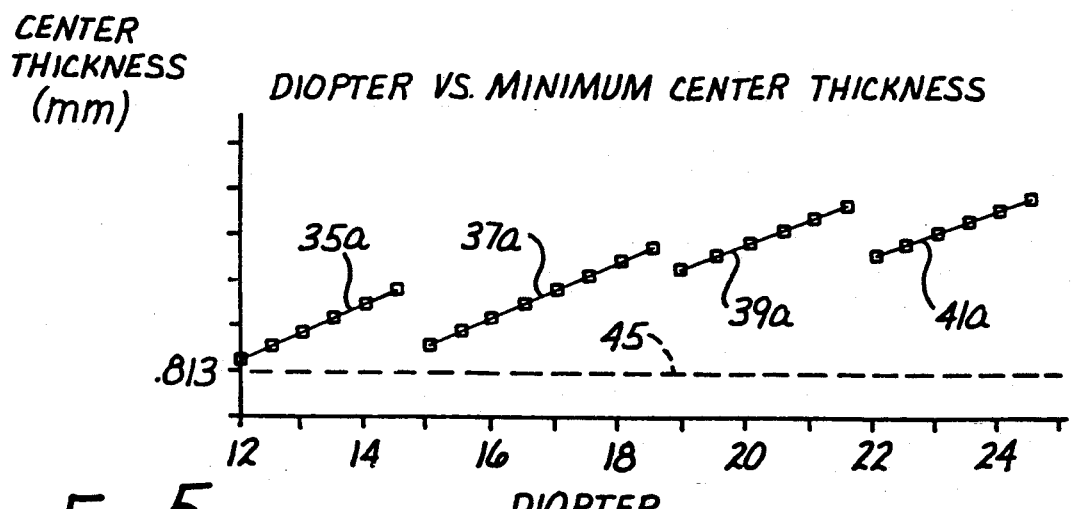
FIG. 5 is a plot of diopter power versus minimum center thickness for several groups of optics.

As stated above, it is preferred to maintain the center thickness of the optic 13 at or above about 0.813 mm in order to provide the desired mechanical strength for the optic while maintaining the maximum cross sectional area no more than about 4.4 square mm. FIG. 5 shows curves 35a, 37a, 39a and 41a, which correspond to the curves 35, 37, 39 and 41, respectively. The curves of FIG. 5 show how the minimum center thickness T1 of the optic 13 increases with diopter power within each of the diopter groups and that the maximum center thickness of the optic is always above the lower limit of 0.813 mm as shown by the lower limit line 45 in FIG. 5.

FIG. 6 illustrates, by way of example, one way that the IOL 11 can be folded for insertion into the eye. In FIG. 6, the optic 13 is folded in half generally about a diameter, and the fold line may be generally along a reference line 47 shown in FIG. 1, although this is purely illustrative. The left half of the optic 13 shown in FIG. 1 is folded under the right half of the optic to provide the folded condition shown in FIG. 6. The fold can be along any desired diameter so as to place the fixation member 15 and 17 in the desired position for insertion. The fixation members 15 and 17 are sufficiently flexible so as not to impede insertion through the incision.

FIG. 7 schematically shows a human eye 51 which includes a natural lens 53 in the capsular bag 55. In order to remove the natural lens 53, a phaco incision 57 in the form of a scleral tunnel incision is formed in the eye as shown by way of example in FIG. 7 and a phaco tip 59 of a conventional phacoemulsification instrument 61 is inserted through the incision into the region of the eye containing the natural lens 53. The incision 57 is ordinarily no more than about 3.2 mm in length and the tissue of the eye typically fairly snugly surrounds the phaco tip 59. Ultrasonic energy provided by the instrument 61 breaks up the natural lens 53 and the lens fragments are aspirated from the capsular bag 55 using subatmospheric pressure applied through the phaco tip 59. After satisfactory removal of the natural lens 53, the phaco tip 59 is withdrawn from the eye 51 through the incision 57.

The next step is to insert the IOL 11 through the incision 57 without lengthening the incision. To accomplish this, the IOL 11 must be appropriately deformed so that the 6 mm diameter optic 13 can fit through a scleral tunnel incision of no more than about 3.2 mm in length. This can be accomplished, by folding of the IOL as shown by way of example in FIG. 6. The folding of the IOL 11 and its insertion through the incision 57 is preferably carried out with an appropriate insertion tool.

Figure 8A:
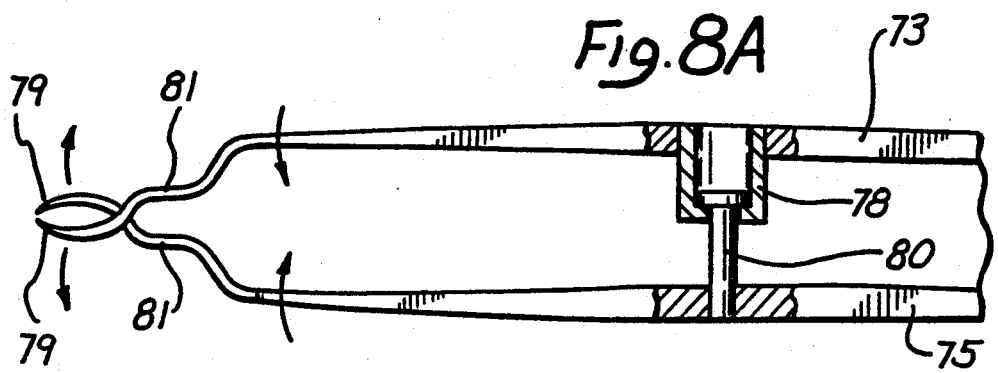
FIG. 8A is a fragmentary plan view partially in section showing the distal portion of the insertion tool.

Various different insertion tools as are known to surgeons in the phacoemulsification and IOL implantation art such as the MacDonald inserter, the Fine inserter, the McPherson forceps or the Tying forceps can be employed. FIG. 8 shows a conventional MacDonald inserter 71 which includes resilient metal arms 73 and 75 joined together at a proximal end portion 77 so that the arms are resiliently urged away from each other. The arms 73 and 75 terminate in tips 79, respectively which are normally held in a closed position in which they are almost in contact with each other by the biasing force acting on the arms. A flanged sleeve 78 and a flanged pin 80 coupled to the arms 73 and 75 respectively form a stop which limits separation of the arms and prevents hard contact of the tips 79. Although the arms 73 and 75 are biased away from each other, the same biasing force urges the tips 79 toward each other by virtue of cross over sections 81 of the arms shown in FIG. 8A. The tips 79 and the cross over sections 81 are relatively rigid but of sufficiently small dimensions to pass through the incision 57 without lengthening of that incision.

The IOL 11 can be folded as shown in FIG. 6 and grasped between the tips 79. The IOL 11 can then be inserted through the incision 57 into the eye as shown schematically in FIG. 9 without enlarging the incision 57. The implantation procedure may be essentially the same as known procedures. Once implanted, the resilient, deformable optic 13 returns to its normal or undeformed condition and the fixation members 15 and 17 fix the IOL 11 in the eye in the usual manner.

Particularly useful silicone based materials are reinforced elastomeric compositions having the chemical composition of a cross-linked copolymer including about 12 to about 18 mol percent of aryl substituted siloxane units of the formula $R_4R_5$-SiO where the aryl substituents ($R_4$ and $R_5$ groups) can be independently selected from phenyl groups, mono- lower alkyl substituted phenyl groups, and di- lower alkyl substituted phenyl groups. Preferably, both aryl groups are simple phenyl, and the resulting diphenyl siloxane unit is present in the copolymer in an amount of about 14 to about 16 mol percent.

The copolymer is end blocked with trisubstituted (monofunctional) siloxane units. At least one substituent of the end blocking group contains an olefinic bond. Thus, the general formula of the end blocking group incorporated in the copolymer is $R_1R_2R_3SiO_{0.5}$ where the nature of the $R_1$ and $R_2$ is not critical, and they may be independently selected from, for example, alkyl, aryl, substituted alkyl and substituted aryl groups. $R_3$ contains an olefinic bond. $R_3$ is preferably an alkenyl group, more preferably a vinyl group. In a preferred embodiment, the end blocking group is a dimethyl, vinyl siloxane unit. The role of the olefinic (vinyl) group is to enable curing or cross-linking of the polymer, and preferably covalently linking certain ultraviolet light absorbing compounds to the cross-linked copolymer matrix.

The balance of the siloxane building blocks of the copolymer is preferably dialkyl siloxane units wherein the two alkyl substituents are either ethyl or methyl. In other words, the general formula of the balance of the siloxane building blocks of the copolymer is preferably $R_6R_7$-SiO where the $R_6$ and $R_7$ groups are independently selected from methyl and ethyl. Preferably both $R_6$ and $R_7$ groups are methyl.

The copolymer may have a degree of polymerization (dp) of about 100 to about 2000, although a degree of polymerization of about 250 is preferred, particularly when the $R_4$ and $R_5$ groups are phenyl and the $R_6$ and $R_7$ groups are methyl.

The preparation of the copolymer having the above described components can be performed in accordance with processes known in the art, from starting materials which are either commercially available or can be made in accordance with well known processes.

The elastomeric silicone composition preferably contains a reinforcer, for example, a fume silica reinforcer, such as trimethylsilyl treated silica reinforcer, finely dispersed therein.

The reinforcer, for example, the fume silica reinforcer, is preferably used in an amount of about 15 to about 45 parts by weight of the reinforcer to 100 parts of the copolymer. Fume silica itself is commercially available. The fume silica reinforcer preferably used has a surface area of about 100 to about 450 meter$^2$/gram. More preferably, the fume silica has a surface area of about 200 meter$^2$/gram, is present in an amount (by weight) of about 27 parts (by weight) to 100 parts (by weight) of the copolymer, and is trimethylsilylated with hexamethyldisilazane substantially in the same step where the copolymer is intimately mixed with the silica.

The intimate mixture of the fume silica with the copolymer is commonly termed the "base" in the art. For the purpose of making materials suitable for intraocular lens, the base may be dispersed in a suitable inert solvent, such as trichlorotri-fluoroethane, and the dispersion filtered to remove any solid impurities. Thereafter, the solvent is removed by gentle heat and vacuum.

In accordance with standard practice in the art, the base is divided into two aliquots which preferably are of equal weight. The aliquots are commonly termed "Part A" and "Part B".

Silicon bonded hydride groups are added to the second aliquot (Part B) in the form of cross-linking agents, which are conventional and well known in the art. The liquid organohydrogen polysiloxane cross linkers having the formula $(R)_a(H)_bSiO_{4-a-b}/2$ wherein R is simple lower alkyl, for example, methyl, and a ranges from about 1.00 to about 2.10 and b ranges from about 0.1 to about 1.0, are eminently suitable.

The platinum catalyst can be selected from materials which are conventional and well known in the art.

The cross-linking should not proceed too rapidly at room temperature, thereby allowing at least two, preferably about six hours for work time with the mixed aliquots. For this reason, a suitable cross-linking inhibitor, such as 1, 2, 3, 4 tetramethyl- 1, 2, 3, 4-tetravinyl cyclotetrasiloxane, may be added to the second aliquot (Part B).

Formation of intraocular lens bodies may be accomplished by liquid injection molding, or by cast or compression molding of the intimately mixed Parts A and B.

Although an exemplary embodiment of the invention has been shown and described, many changes, modifications, and substitutions may be made by those having ordinary skill in the art without departing from the spirit and scope of this invention.

We claim:

1. An intraocular lens for implantation in an eye comprising:
    a resilient, deformable silicone based optic having at least about 20 diopter power, said optic having a periphery and being configured so that the optic can be resiliently deformed from a normal optical condition into a deformed insertion condition to permit the intraocular lens to be passed through a scleral tunnel incision of no longer than about 3.2 millimeters into the eye;
    fixation means coupled to the optic for retaining the optic in the eye; and
    said optic when implanted in the eye being in the normal optical condition and having sufficient rigidity to be substantially free of optical distortion resulting from force from the eye acting on the intraocular lens and said optic when implanted in the eye being of sufficient size to substantially prevent glare resulting from interaction of light and the periphery of the optic.

2. An intraocular lens as defined in claim 1 wherein the optic has a maximum cross sectional area of no greater than about 4.4 square millimeters.

3. An intraocular lens as defined in claim 1 wherein the optic has an index of refraction of at least about 1.445.

4. An intraocular lens as defined in claim 1 wherein the optic has an elongation of at least about 200 percent.

5. An intraocular lens as defined in claim 1 wherein the optic has an optical axis and the thickness of the optic along said axis is no less than about 0.736 millimeters.

6. An intraocular lens as defined in claim 1 wherein the optic has an optical axis, a central optical zone and a peripheral zone circumscribing the optical zone and the thickness of the peripheral zone in the axial direction is no less than about 0.305 millimeters.

7. An intraocular lens as defined in claim 1 wherein the optic has a maximum cross sectional area of no greater than about 4.4 square millimeters and the optic has an index of refraction of at least about 1.46.

8. An intraocular lens for implantation in an eye comprising:
    a resiliently deformable silicone based optic having a maximum cross sectional area of no greater than about 4.4 square millimeters and an index of refraction of at least about 1.445, said optic being configured so that the optic can be resiliently deformed from a normal optical condition into a deformed insertion condition to permit the intraocular lens to be passed through a scheral tunnel incision of no longer than about 3.2 millimeters into the eye;
    fixation means coupled to the optic for retaining the optic in the eye; and
    said optic when implanted in the eye being in the normal optical condition and having sufficient rigidity to be substantially free of optical distortion resulting from force from the eye acting on the intraocular lens and said optic when implanted in the eye being of sufficient size to substantially prevent glare resulting from interaction of light and the periphery of the optic.

9. An intraocular lens as defined in claim 8 wherein the optic has an elongation of at least about 260 percent.

10. An intraocular lens as defined in claim 8 wherein the optic is generally circular and has a diameter of at least about 6 millimeters.

11. An intraocular lens as defined in claim 8 wherein the fixation means includes first and second generally C-shaped resilient fixation members coupled to the optic at generally diametrically opposed locations.

12. An intraocular lens for implantation in an eye comprising:

a generally circular resilient, deformable silicone based optic having a maximum cross sectional area of no greater than about 4.4 square millimeters, an index of refraction of at least about 1.445, a diopter power in the range of from about $12d$ to about $24d$ and a diameter of at least about 5 millimeters;

said optic having anterior and posterior faces, at least one of said faces being convex; and fixation means for retaining the optic in the eye.

13. An intraocular lens as defined in claim 12 wherein the optic has an elongation of at least about 200 percent.

14. An intraocular lens for implantation in an eye comprising:

a generally circular resilient, deformable optic having an elongation of at least about 200 percent, a maximum cross sectional area of no greater than about 4.4 square millimeters, an index of refraction of at least about 1.445, a diopter power in the range of from about $12d$ to about $24d$ and a diameter of at least about 5 millimeters;

said optic having anterior and posterior faces, at least one of said faces being convex; and fixation means for retaining the optic in the eye.

15. An intraocular lens as defined in claim 14 wherein the optic has a diopter power of at least about $20d$.

16. A set of intraocular lenses for implantation in eyes, said set of intraocular lens comprising:

first, second, third and fourth intraocular lenses;

each of said first, second, third and fourth intraocular lenses including a resilient, deformable silicone based optic configured so that the optic can be deformed to permit the intraocular lens to be passed through a scleral tunnel incision of no longer than about 3.2 millimeters into the eye and fixation means for retaining the optic in the eye, each of said optics having a periphery and when implanted in the eye having sufficient rigidity to be substantially free of optical distortion resulting from force from the eye acting on the intraocular lens and each of said optics when implanted being of sufficient size to substantially prevent glare resulting from interaction of light on the periphery of the optic; and said optics of said first, second, third and fourth intraocular lenses having diopter powers in the ranges of from about $12d$ to about $14.5d$ from about $15d$ to about $18.5d$ from about $19d$ to about $21.5d$ and from about $22d$ to about $24d$ respectively.

17. A set of intraocular lenses as defined in claim 16 wherein each of the optics has a maximum cross sectional area no greater than about 4.4 square millimeters.

18. A set of intraocular lenses as defined in claim 17 wherein each of the optics has an index of refraction of at least about 1.46.

19. A set of intraocular lenses as defined in claim 18 wherein each of the optics has an elongation of at least about 200 percent.

20. A set of intraocular lenses as defined in claim 18 wherein each of the optics has an optical axis, a central optical zone and a peripheral zone circumscribing the optical zone and the thickness of the peripheral zone in the axial direction is no less than about 0.305 millimeter.

21. A set of intraocular lenses as defined in claim 20 wherein the optics of the first, second, third and fourth intraocular lens have thickness of the peripheral zones of no less than about 0.457 millimeter, 0.381 millimeter, 0.381 millimeter and 0.381 millimeter, respectively, and generally circular optical zones with diameters of at least about 5.5 millimeters, 5.5 millimeters, 5.25 millimeters and 5 millimeters, respectively.

22. An intraocular lens for implantation in an eye comprising:

a resiliently deformable silicone based optic having a maximum cross sectional area of no greater than about 4.4 square millimeters and an elongation of at least about 260 percent, said optic being configured so that the optic can be resiliently deformed from a normal optical condition into a deformed insertion condition to permit the intraocular lens to be passed through a scleral tunnel incision of no longer than about 3.2 millimeters into the eye;

fixation means coupled to the optic for retaining the optic in the eye; and said optic when implanted in the eye being in the normal optical condition and having sufficient rigidity to be substantially free of optical distortion resulting from force from the eye acting on the intraocular lens and said optic when implanted in the eye being of sufficient size to substantially prevent glare resulting from interaction of light and the periphery of the optic.

* * * * *